US00PP27002P3

(12) United States Plant Patent
Suphachadiwong

(10) Patent No.: US PP27,002 P3
(45) Date of Patent: Aug. 2, 2016

(54) ***DENDROBIUM* ORCHID PLANT 'SPCDW1005'**

(50) Latin Name: ***Dendrobium* hybrid**
Varietal Denomination: SPCDW1005

(71) Applicant: Thumrong Suphachadiwong, Chonburi (TH)

(72) Inventor: Thumrong Suphachadiwong, Chonburi (TH)

(73) Assignee: Suphachatwong Innovations, Ltd (TH)

( * ) Notice: Subject to any disclaimer, the term of this patent is extended or adjusted under 35 U.S.C. 154(b) by 191 days.

(21) Appl. No.: 13/999,298

(22) Filed: Feb. 6, 2014

(65) Prior Publication Data

US 2014/0223626 P1 Aug. 7, 2014

(30) Foreign Application Priority Data

Feb. 7, 2013 (QZ) ..... A201300222

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
(74) *Attorney, Agent, or Firm* — Cassandra Bright

(57) ABSTRACT

A new and distinct *Dendrobium* cultivar named 'SPCDW1005' is disclosed, characterized by distinctive petal and sepal shape, unique petal and sepal color and predominantly purple lip color. The new variety is a *Dendrobium*, typically produced as an indoor ornamental plant.

1 Drawing Sheet

Latin name of the genus and species: *Dendrobium* hybrid.
Variety denomination: 'SPCDW1005'.

BACKGROUND OF THE INVENTION

This application relates to a new cultivar of *Dendrobium* hybrid. The new variety is the product of a planned breeding program. The new variety originated as a seedling from the crossing of the unpatented, proprietary seed parent *Dendrobium* 'BJ' with the unpatented, proprietary pollen parent referred to as *Dendrobium* '181N'. The crossing was made by the inventor in his research greenhouse in Chonburi, Thailand in December of 1999.

The new variety was first selected by the inventor, Thumrong Suphachadiwong, a citizen of Thailand, in February of 2003 in a research greenhouse belonging to the inventor in Chonburi, Thailand. After identifying the new variety as a potentially interesting selection, the inventor continued confidential testing and propagation of 'SPCDW1005', assessing stability of the unique characteristics of this variety.

Asexual reproduction of the new cultivar 'SPCDW1005' was first performed at a commercial laboratory belonging to the inventor in Chonburi, Thailand by tissue culture, using meristem culture in September of 2005. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SPCDW1005' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1005'. These characteristics in combination distinguish 'SPCDW1005' as a new and distinct *Dendrobium* cultivar:

1. Distinctive petal and sepal shape.
2. Green with purple sepal and petal color.
3. Predominantly purple lip color.

PARENT COMPARISON

Plants of the new cultivar 'SPCDW1005' are similar to the seed parent, *Dendrobium* 'BJ' in most horticultural characteristics. However the new variety, 'SPCDW1005' differs from 'BJ' in the following characteristics:

1. Different flower color.
2. More compact grow habit.
3. Smaller flower size.

Plants of the new cultivar 'SPCDW1005' are similar to the pollen parent, *Dendrobium* '181N' in most horticultural characteristics. However the new variety, 'SPCDW1005' differs from '181N' in the following characteristics:

1. Different flower color.
2. Much larger plant size.
3. Much larger flower size.

COMMERCIAL COMPARISON

'SPCDW1005' is similar in most horticultural characteristics to the unpatented commercial variety *Dendrobium* 'SPCDW0508' in most horticultural characteristics. However the new variety, 'SPCDW1005' differs from 'SPCDW0508' in the following characteristics:

1. Different sepal and pedal color.
2. Glossier leaves.
3. Pedal and sepal shape is rounder.
4. The lateral lobes of the lips are more open.
5. Different lip color.
6. Color pattern shows more netting.

Plants of the new cultivar 'SPCDW1005' are also comparable to the unpatented commercial variety *Dendrobium* 'SPCDW1013'. The two *Dendrobium* varieties are similar in most horticultural characteristics; however, the new variety 'SPCDW1005' differs in the following ways:

1. Different sepal and pedal color.
2. Different lip color.
3. Pedal and sepal shape is rounder.

BRIEF DESCRIPTION OF THE PHOTOGRAPH

The accompanying photograph in FIG. 1 illustrates in full color a typical plant of 'SPCDW1005' grown in a commercial greenhouse in Honselersdijk, the Netherlands. The plant is 1 years old from a rooted cutting, in a 10.5 cm pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1005' plants grown in a commercial greenhouse in Honselersdijk, the Netherlands. The plant is 1 year old from a rooted cutting, in a 10.5 cm pot. Temperatures ranged between 26° C. and 30° C. day and night. No photoperiodic or chemical treatments were given to the plants. The light sum was set at 5 moles per day and the plant was given shading and artificial light in order to come to the light sum of 5 moles per day. Both shading and artificial lightning were frequently applied in order to achieve the ideal light sum of 5 moles per day. Measurements and numerical values represent averages of typical plant types.

Botanical classification: *Dendrobium* hybrid. 'SPCDW1005'.

PROPAGATION

Type of propagation typically used: Tissue culture, using meristem culture. The very growing center of a new growth bud is taken and grown on by agitating constantly in a special nutrient rich liquid until the cell mass is large enough to be split in to small sections these are then either grown on in to plants or the process is repeated to produce more tissue for growing on. This method is often used to mass produce a specific hybrid for commercial purposes.

Time to initiate roots: Tissue culture takes 18 months. After deflasking it takes another 9 to 12 months to get a well-rooted plant under average temperatures ranging between 26 en 30 degrees Celsius. After planting in the end pot, the young plant already has roots and those roots continue to grow in the end pot almost right away and certainly within 8 days.

Time to produce a rooted cutting/liner: Tissue culture takes 18 months. After deflasking it takes another 9 to 12 months to get a well-rooted plant under average temperatures ranging between 26 en 30 degrees Celsius. After planting in the end pot, the young plant already has roots and those roots continue to grow in the end pot almost right away and certainly within 8 days.

Root description:

*Root color*.—White near RHS NN155B.
*Average diameter*.—Average: 0.2 cm.
*Average length*.—Lateral roots average: 5.2 cm.

PLANT

Growth habit: Sympodial, upright.
Height from top of soil line to top of foliage: 29.4 cm.
Height from top of soil line to top of flowers: 55.4 cm.
Plant spread: 22.4 cm.
Normal pot size: 10.5 cm circular pot.
Growth rate: Moderate.
Number of leaves per plant: Average: 42.
Plant stem:

*Length*.—Approximately 12.5 cm.
*Diameter*.—Approximately 1.7 cm.
*Aspect*.—Approximately 75° angle to soil surface (=0°).
*Strength*.—Strong.
*Texture*.—Glabrous, very slightly glossy, axially ribbed.
*Color*.—Yellow-green, in between near RHS N144A and 152C.
*Pseudobulb*.—Longitudal section shape: Lanceolate to narrow elliptic. Cross section shape: Elliptic to near circular.

FOLIAGE

Leaf:

*Arrangement*.—Distichous.
*Average length*.—Approximately 12.0 cm.
*Average width*.—Approximately 5.8 cm.
*Shape of blade*.—Ovate to narrow ovate.
*Aspect*.—Leaves in an average angle of 75° to main stem (=0°).
*Apex*.—Acute.
*Base*.—Sheathing.
*Sheath length*.—Average 2.7 cm. Sheath width: Average 1.6 cm. Sheath color: Yellow-green, near RHS 146D, slightly striped axially, yellow-green; near RHS 147B.
*Margin*.—Entire.
*Texture of top surface*.—Glabrous, glossy.
*Texture of bottom surface*.—Glabrous, moderately glossy.
*Durability to physical stress*.—High.
*Color*.—Young foliage upper side: Green to yellow-green; in between near RHS 143A and 144A but darker. Young foliage under side: Yellow-green; near RHS 144A. Mature foliage upper side: Green; in between near RHS N137A and 143A but darker. Mature foliage under side: Yellow-green; near RHS 146A.
*Venation*.—Type: Parallel. Venation coloration: Upper Surface: Green; in between near RHS N137A and 143A but darker. Lower Surface: Yellow-green; near RHS 146A.

Petiole: No petioles present.

FLOWERING CHARACTERISTICS

Flower bud:

*Rate of opening*.—Approximately 30 days from first sight.

*Length*.—Approximately 2.4 cm.

*Diameter*.—Approximately 1.1 cm.

*Shape*.—Ovate, curved.

*Color*.—Yellow-green; in between near 145A and 145B, margins of unopened sepals and spur red-purple; near RHS 61A.

Peduncle:

*Length*.—Approximately 29.9 cm.

*Diameter*.—Approximately 0.3 cm.

*Aspect*.—Approximately 0° angle to stem.

*Strength*.—Strong.

*Texture*.—Glabrous, slightly glossy.

*Color*.—Yellow-green; near RHS 146C.

Inflorescence:

*Flowers per stem*.—Average: 13.

*Inflorescence arrangement*.—Simple raceme. Individual flowers positioned along peduncle.

*Inflorescence height*.—Approximately 19.1 cm (from lowest pedicel to top of inflorescence).

*Inflorescence width*.—Approximately 8.5 cm.

Individual flower:

*Flower type*.—Single, orchidaceous (zygomorphic), typical for *Dendrobium*.

*Rate of opening*.—After the first flower has opened, it takes approximately four weeks before the top flower opens.

*Lastingness*.—Individual flowers can last up to 9 weeks on the plant.

*Shape*.—Orchidaceous (zygomorphic), typical for *Dendrobium*, with three sepals, two lateral petals and a labellum (third petal).

*Height*.—Approximately 4.6 cm.

*Diameter*.—Approximately 5.1 cm.

*Depth*.—Approximately 2.3 cm.

*Fragrance*.—No fragrance.

*Persistent*?.—Non-persistent.

*Quantity of petals*.—Average: 3 (two lateral petals and a labellum (=third petal)) Only the two lateral petals are described here as such.

Petals:

*Arrangement*.—Oppositely placed on each side of the column.

*Length*.—Approximately 2.8 cm.

*Width*.—Approximately 1.9 cm.

*Shape*.—Obovate, slightly curved.

*Apex*.—Rounded.

*Base*.—Cuneate.

*Margin*.—Entire.

*Appearance*.—Both sides matte, velvety.

*Texture, upper forward surface*.—Glabrous, velvety.

*Texture, lower back surface*.—Glabrous, velvety.

*Color*.—When opening, forward surface: Yellow-green; in between near RHS 145A to 145B and 146A, veins and margins red-purple; near RHS 71A, base lighter; near RHS 71B. When opening, back surface: Yellow-green; RHS 145B, veins and margins purple; near RHS N77B. Fully Opened, forward surface: Yellow-green; RHS 145C, veins and margins red-purple; near RHS 72B, base slightly darker; near RHS 72A. Fully Opened, back surface: Yellow-green; RHS 145C, veins and margins purple; near RHS N78C. Fading, forward surface: not fading (colours similar to "Fully Opened"). Fading, back surface: not fading (colours similar to "Fully Opened").

*Color venation fully opened, forward surface*.—As surface (colours similar to "Fully Opened").

*Color venation fully opened, back surface*.—As surface (colours similar to "Fully Opened").

Labellum:

*Shape*.—Deltoid, three-lobed, strongly involute. 2 lateral lobes and 1 apical lobe.

*Length*.—Approximately 1.8 cm.

*Width*.—Approximately 1.6 cm (when "folded open", approximately 2.6 cm).

Lateral lobe:

*Shape*.—Obovate.

*Length*.—Average 1.4 cm.

*Width*.—Average 1.0 cm.

*Tip*.—Rounded.

*Base*.—Broad cuneate.

*Texture*.—Glabrous, velvety.

*Appearance*.—Matte, moderately velvety.

*Margin*.—Entire.

*Color*.—When opening, forward surface: Near RHS Purple N79B, base lighter; near RHS N79C. When opening, back surface: Near RHS Purple N79B and N79C. Fully Opened, forward surface: Near RHS Purple N79B. Fully Opened, back surface: Near RHS Purple N79B. Fading, forward surface: Near RHS Purple N79B. Fading, back surface: Near RHS Purple N79B.

*Venation coloration*.—Visible on back surface of fully opened flower. Colored near Purple N79B. Venation not visible on front surface.

Apical lobe:

*Shape*.—Narrow obovate.

*Length*.—Average 2.3 cm.

*Width*.—Average 1.3 cm.

*Tip*.—Rounded.

*Base*.—Broad cuneate.

*Color*.—When opening, forward surface: Near Yellow-Green 146D. Densely veined near Purple N79B and N79C. When opening, back surface: Near RHS Yellow-Green; 145D. Apex purple; near RHS N79B. Fully Opened, forward surface: Near RHS Purple N79B, slightly blotched, in between veins Yellow-Green 146D. Base near RHS Purple N79C. Fully Opened, back surface: Near RHS Yellow-Green 145D. Apex purple; near RHS N79B. Fading forward surface: Near RHS Purple N79B, slightly blotched, in between veins Yellow-Green 146D. Base near RHS Purple N79C. Fading, back surface: Near RHS Yellow-Green 145D. Apex purple; near RHS N79B.

*Venation coloration*.—Present on front surface of fully opened flower. Colored near Purple N79B. Venation not visible on back surface.

*Callosites*.—Dimensions: Average: 0.6 cm long and 0.5 cm wide. Location: central placed on the labellum, coloured purple; near RHS N79A to N79B.

*Lip eye*.—Absent.

*Lip twisting*.—Absent.

*Lip undulation*.—Absent.
*Lip fringing of the margin*.—Absent.
*Lip pubescence*.—Absent.

Sepals:
*Quantity*.—Average: 3.
*Appearance*.—Matte, velvety.
*Length*.—Approximately 2.8 cm.
*Width*.—Dorsal sepal, approximately 1.2 cm. Lateral sepals; approximately 1.4 cm.
*Shape*.—Narrow ovate, dorsal sepal oblong, slightly curved.
*Apex*.—Acute.
*Base*.—Broad cuneate.
*Margin*.—Entire, without twisting or undulation.
*Texture*.—Glabrous, velvety.
*Color*.—Forward surface: Yellow-green; near RHS 145B, margins, base and outer tip purple; near RHS N78C, veined darker; near RHS N78B. Back surface: Yellow-green; near RHS 145C, margins and base purple; Near RHS N78C.
*Mentum*.—Average width: 0.7 cm. Average length: 0.5 cm. Color: Near RHS Greyed-Purple 185C, tip near 187B and 187C.

Pedicels:
*Length*.—Approximately 3.9 cm.
*Diameter*.—Approximately 0.2 cm.
*Angle*.—Approximately 60° angle to peduncle (=0°).
*Strength*.—Moderately strong.
*Texture*.—Glabrous, moderately glossy.
*Color*.—Yellow-green; near RHS 145C, base darker; 145A to 145B.

REPRODUCTIVE ORGANS

Stamens, style and stigma fused into column?: Yes.
*Column length*.—Average: 0.6 cm.
*Column diameter*.—Average: 0.7 mm.
*Column color*.—Purple; near RHS N79B to N79C.

Anther cap:
*Average width*.—0.3 cm.
*Average length*.—0.2 cm.
*Color*.—Near RHS White N155A.
*Ovary*.—Position: Superior, placed directly above stigma. Diameter: Average: 0.2 cm. Color: Purple; near RHS N79B to N79C.
*Stigma*.—Shape: Clavate. Color: Green-white; near RHS 157A. Dimensions: Average: 0.3 cm high and 0.3 cm wide.
*Pollinia*.—Color: Yellow-orange; near RHS 14A. Dimensions: Average: 0.075 cm long and 0.1 cm wide. Quantity: 2.

OTHER CHARACTERISTICS

Disease and pest resistance: High tolerance for typical diseases and pests of *Dendrobium*.
Drought tolerance and cold tolerance: Normal for Genus.
Fruit/seed production: No fruits/seeds detected to date.

What is claimed is:

1. A new and distinct cultivar of *Dendrobium* plant named 'SPCDW1005' as herein illustrated and described.

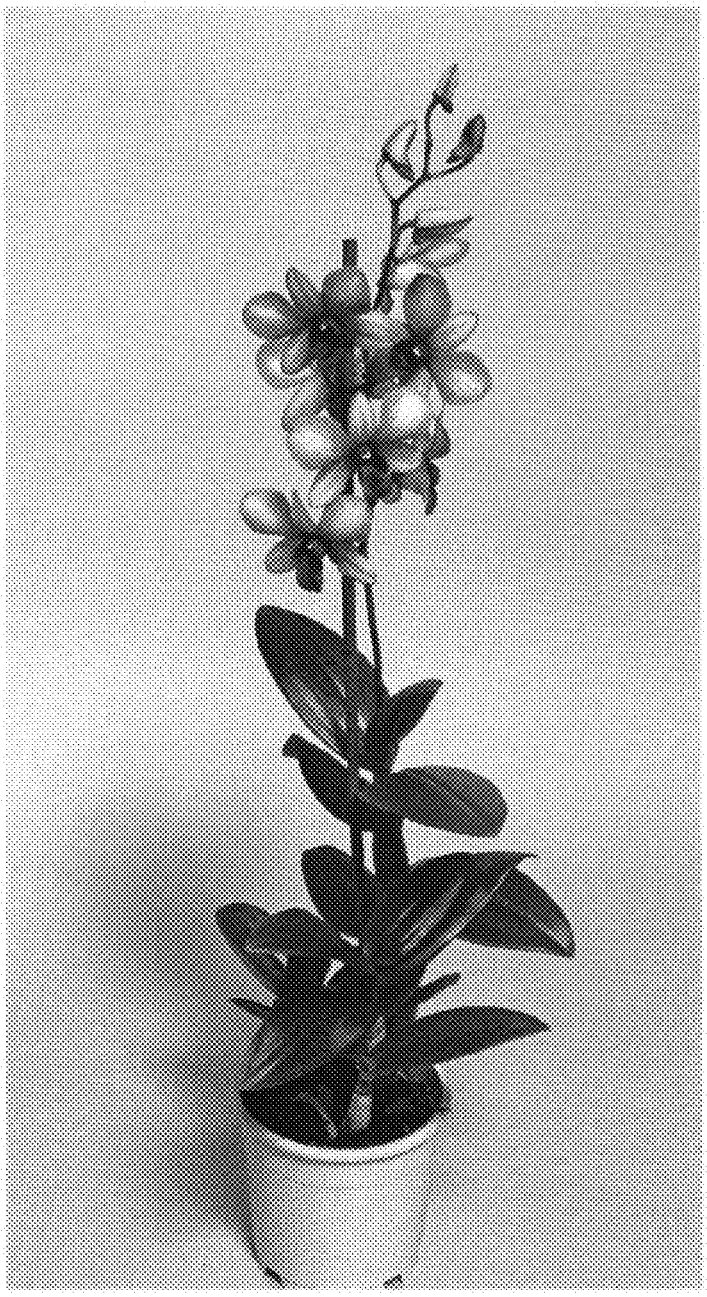

* * * * *